United States Patent [19]

Slocum

[11] Patent Number: 4,759,351

[45] Date of Patent: Jul. 26, 1988

[54] OSTEOTOMY METHOD FOR BIOMECHANICAL FEMORAL NECK LENGTHENING AND TORSION

[76] Inventor: D. Barclay Slocum, 241 Spy Glass Dr., Eugene, Oreg. 97401

[21] Appl. No.: 946,863

[22] Filed: Dec. 29, 1986

[51] Int. Cl.$^4$ ................................................ A61F 5/04
[52] U.S. Cl. ............................ 128/92 VY; 128/92 YK
[58] Field of Search ...... 128/92 VY, 92 VV, 92 VW, 128/92 YJ

[56] References Cited

U.S. PATENT DOCUMENTS

| | | | |
|---|---|---|---|
| 3,486,500 | 12/1969 | Ball et al. | 128/92 YK |
| 4,335,715 | 6/1982 | Kirkley | 128/92 VY |
| 4,421,112 | 12/1983 | Mains et al. | 128/92 VY |
| 4,433,681 | 2/1984 | Comparetto | 128/92 VY |
| 4,565,191 | 1/1986 | Slocum | 128/92 VY |

Primary Examiner—Stephen C. Pellegrino
Assistant Examiner—Colleen M. Reilly
Attorney, Agent, or Firm—Kolisch, Hartwell & Dickinson

[57] ABSTRACT

A method of performing a femoral neck-lengthening osteotomy is disclosed. A cut is made in the proximal end of the femur, generally parallel with the sagittal plane and substantially bisecting the proximal end of the femur. The resulting, relatively movable femoral sections are diverged to lengthen the femoral neck. In a modification, the femoral neck is also torsed by relative rotation of the two femoral sections. A wedge is inserted between the thus-diverged and, optionally, rotated sections, and the desired configuration is fixed in a suitable manner.

11 Claims, 2 Drawing Sheets

OSTEOTOMY METHOD FOR BIOMECHANICAL FEMORAL NECK LENGTHENING AND TORSION

BACKGROUND AND SUMMARY OF THE INVENTION

This invention relates generally to an osteotomy technique, and more particularly to a method for performing a femoral osteotomy. A preferred manner of practicing the invention is described in conjunction with veterinary surgery on the leg of a dog.

Hip dysplasia is a painful and frequently disabling condition of instability between the acetabulum and the femoral head. It usually results from insufficient formation of the acetabulum, which is the cup-shaped socket that receives the femoral head. As the hip is a load-bearing joint, instability in the positional relationship of the acetabulum and the femoral head frequently results in further injury to surrounding tissue.

Surgical techniques for correcting hip dysplasia have been suggested, notably the pelvic osteotomy. In that procedure, an acetabular segment is rotated to allow the underformed acetabulum better to "cover" the femoral head. This is an invasive procedure requiring at least three pelvic incisions. Conventional fixation plates are incapable of withstanding the shear and torque forces incident to acetabular segment rotation, resulting in loss of fixation. Bowel and urinary tract complications frequently result from constriction of the pelvic canal. Worse, a pelvic osteotomy performed by a skilled surgeon often fails to correct the instability between the acetabulum and the femoral head. That is because rotation of the acetabular segment to "cover" the femoral head typically does little to compensate for the joint capsule stretched by the dysplastic process.

It has been discovered that merely lengthening the biomechanical femoral neck—referred to herein as the femoral neck—will, in many cases, correct hip dysplasia. When the femoral neck is lengthened, the femoral head may be fitted more deeply within the acetabulum (even an underformed one), thus stabilizing the joint without resort to a pelvic osteotomy. It has also been discovered that improved results may be obtained from a pelvic osteotomy, when performed in combination with a femoral neck-lengthening osteotomy. A relatively simple and less invasive femoral neck-lengthening osteotomy procedure would then obviate the pelvic osteotomy procedure in some cases, and complement it in others.

In a related syndrome, the proximal end of the femur is found to be rotated about the long axis with respect to the distal end. Successful stabilization of the coxofemoral joint depends upon properly aligning, as well as positioning, the acetabulum and the femoral head. A femoral neck-lengthening osteotomy procedure that allowed preferably concurrent lengthening of the femoral neck and resolving of this torsional deformation would then permit stabilization of the coxofemoral joint even in the case of the twisted femur.

Osteotomies have been used to correct a variety of bone malformations. Intentionally in some cases, and incidentally in others, performance of an osteotomy results in a discontinuity in the median axis of, for example, the tibia or femur. That is a frequently undesirable result, as it tends to weaken these load-bearing members. In order to maximize the post operative, load-bearing capacity of the affected member, a femoral neck-lengthening osteotomy procedure capable of preserving the continuity of the femur's median axis is desirable.

The present invention discloses a technique whereby the femoral neck may be lengthened and, optionally, torsed to relieve the condition of hip dysplasia. As used herein, the coined term "torse" derives from the noun torsion, and means to pivot, relative to the acetabulum, or to twist about the median femoral axis, relative to the distal end of the femur.

A principal object of the invention is to provide an osteotomy technique that lengthens the femoral neck to restore the proper positional relationship between the femoral head and the acetabulum.

Another important object of the invention is to provide an osteotomy technique that torses the femoral neck to restore the proper angular relationship among the femoral head, insertion of the internal and external rotator muscles of the hip and the acetabulum.

A further object of the invention is to provide a technique that accomplishes both the lengthening and torsing of the femoral neck in a single surgical procedure.

Still another object of the invention is to provide a technique that achieves these objects while maintaining the continuity of the femur's median axis.

According to a preferred method of practicing the invention, a cut is made in the proximal end of the femur. The cut is made generally parallel with the sagittal plane. The cut is positioned substantially to bisect the proximal end of the femur over a predetermined distance, creating two relatively movable femoral portions. The femoral portions are then diverged relative to one another by the desired corrective distance. Finally, the femoral portions are fixed in any suitable manner against further relative movement. The femoral neck is thereby lengthened to stabilize its load-bearing relationship with the acetabulum.

According to a modification of this preferred method of practicing the invention, a cut is made as described above, except that the cut is terminated at an angle in the plane of the cut. The modified cut thus extends farther in the cranial region of the femur than it does in the caudal region. While the thus-cut femoral portions are diverged, they are also rotated relative to one another through the desired corrective angle. Fixation is accomplished as described above. By this modified technique, the femoral neck is lengthened and also torsed to correct any femoral malformation and to ensure proper alignment of the femoral head and the acetabulum.

By either the preferred or modified method of practicing the invention, a single planar cut in the femur allows a range of divergence and relative rotation of the cut femoral portions to achieve the desired degree of lengthening and torsing of the femoral neck.

These and other advantages and features of the invention will become more fully apparent when the detailed description below is read with reference to the accompanying drawings.

DETAILED DESCRIPTION OF THE INVENTION

Figure 1:
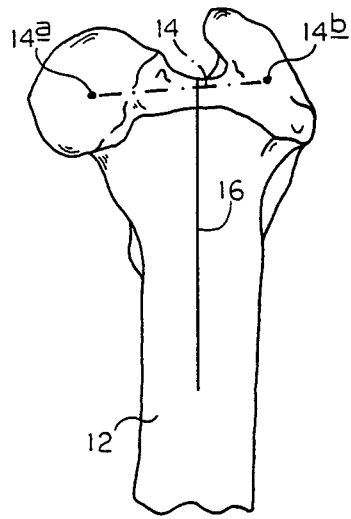
FIG. 1 is a fragmentary side elevation showing a proximal region of a canine femur at an early stage during performance of the invention, and particularly, just following that stage during which a planar cut has been formed in the cranioproximal region of the femur.

Referring first to FIG. 1, the proximal region of a canine femur is indicated at 12. Shown at 14 is the biomechanical femoral neck, defined as the distance between the center 14a of the femoral head and the point 14b in the greater trochanter of the application of all forces incident upon the greater trochanter. In other words, the biomechanical femoral neck may be thought of as a moment arm extending from the center of the femoral head. At 16 a cut is made generally parallel with the sagittal plane. The cut is positioned substantially to bisect the proximal end of the femur, and is dimensioned distally to extend a predetermined distance. In the preferred method of practicing the invention, the cut terminates in a line generally perpendicular to the long axis of the femur. It will be appreciated that treatment of the proximal end of the femur to create joined, relatively movable femoral sections may be accomplished by methods other than cutting.

Figure 2:
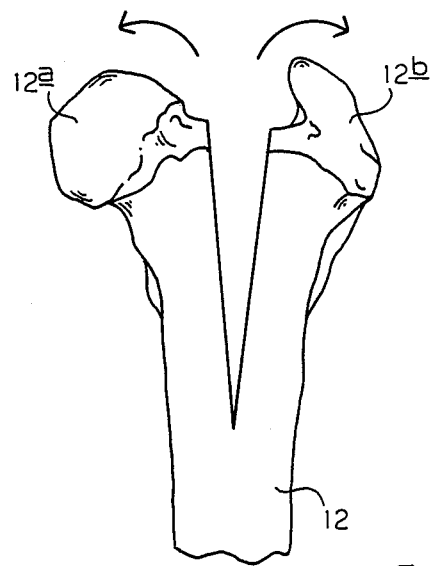
FIG. 2 is similar to FIG. 1, except that it shows a slightly later stage in the performance of the invention in which the cut femoral portions are diverged relative to one another to lengthen the femoral neck.
Figure 3:
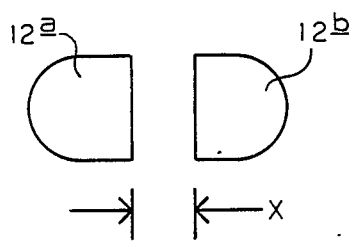
FIG. 3 is a schematic representation of a top view of the cut/diverged femoral portions.
Figure 4:
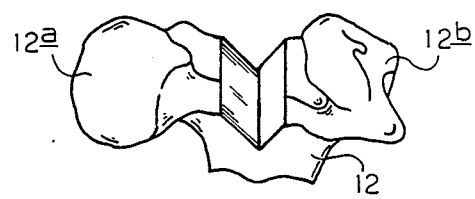
FIG. 4 is a fragmentary top view corresponding to FIG. 2.

After the proximal end of the femur is treated, as by cutting, the femoral sections are adjusted to produce a desired configuration. FIG. 2 shows the adjustment of joined, relatively movable sections 12a and 12b by diverging them relative to one another. In the preferred method of the invention illustrated, femoral sections 12a and 12b are diverged to lengthen the femoral neck 14. FIG. 3 schematically illustrates divergence of the extreme proximal ends of femoral sections 12a and 12b over a predetermined distance X. The dimension X is determined by the amount of lengthening needed in the femoral neck. FIG. 4 is a fragmentary, true-to-life, top view of the femur immediately after the diverging step. This view shows, incidentally, the natural curvature of the femur in its proximal region 12. It will be appreciated that adjusting the femoral sections may be accomplished by methods other than diverging.

Figure 5:
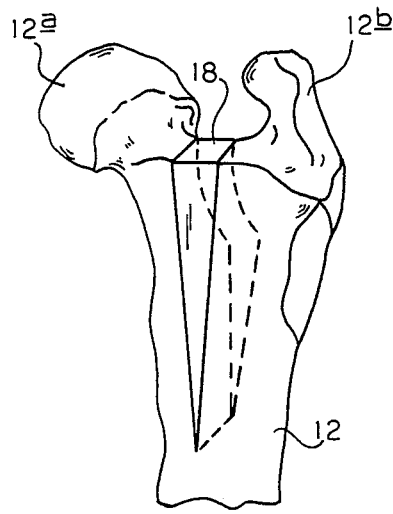
FIG. 5 is an isometric view of the cut/diverged femoral portions, showing a later stage in the performance of the invention in which a wedge is inserted between the femoral portions.

Turning attention to FIG. 5, the next step of the procedure is shown. After cutting, and either during or after diverging the femoral sections, a wedge 18 is inserted between them. The wedge may be of any suitable material, e.g., plastic. In the preferred method of practicing the invention, the wedge is dimensioned to taper from a predetermined lateral dimension X, as illustrated in FIG. 3, to the distal line of the cut. It will be appreciated that, depending upon its material content, wedge 18 might not extend fully from the top to the bottom of cut 16, as such may occlude regenerative blood flow and inhibit healing. It will be appreciated also that wedging the femoral sections may be accomplished by methods other than inserting a wedge.

Figure 6:
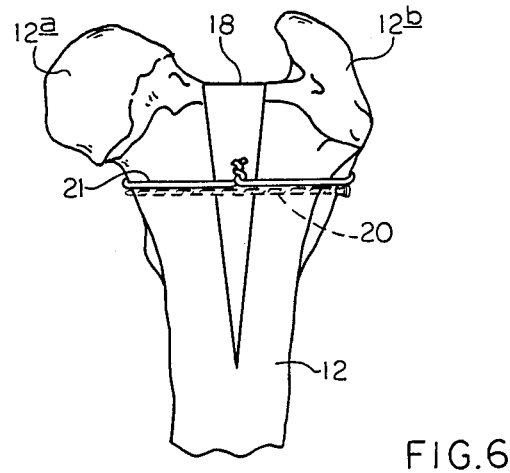
FIG. 6 is similar to FIG. 2, except that it shows the final stage in the procedure of the invention in which the cut/diverged femoral bone sections are fixed against further relative movement.

FIG. 6 shows the final step of the procedure embodied by this invention. The desired configuration of femoral sections 12a and 12b is fixed by screw 20 and wire 21 that prevent their further relative movement. It will be appreciated that fixing the femoral sections may be accomplished by other methods, such as pinning and/or wiring.

As most completely illustrated in FIG. 6, the preferred method of practicing this invention is disclosed, in which relatively diverged femoral sections are fixed to produce a lengthened femoral neck in a canine. The lengthened femoral neck serves to stabilize the load-bearing joint either in conjunction with, or as an alternative to the practice of a pelvic osteotomy.

When it is desired to torse, as well as lengthen the femoral neck, proximal sections may be rotated relative to one another about an axis which generally parallels the long axis of the femur. By the practice of the present invention, this relative rotating may be performed concurrently with the lengthening of the femoral neck. In a preferred practice of this modification, the cut is terminated at an angle in the plane of the cut not generally perpendicular to the long axis of the femur. This modified cut facilitates relative rotation of the femoral sections. It will be appreciated that the cut need not be planar; e.g. it may begin generally parallel with the sagittal plane and spiral as it extends distally along the femur.

Figure 7:
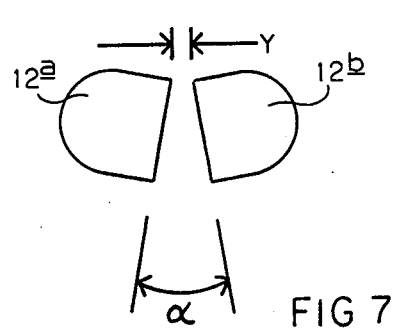
FIG. 7 is a schematic representation similar to FIG. 3, except that it shows a modification to the preferred method of practicing the invention in which the cut femoral portions are diverged and rotated relative to one another to lengthen and torse the femoral neck.

In FIG. 7 this modification to the preferred practice of the invention is illustrated schematically. The femoral sections are shown diverged in their extreme proximal ends over a predetermined distance Y, and are shown rotated relative to one another through a predetermined angle α. The angle α is determined by the amount of torsing needed in the femoral neck.

Figure 8:
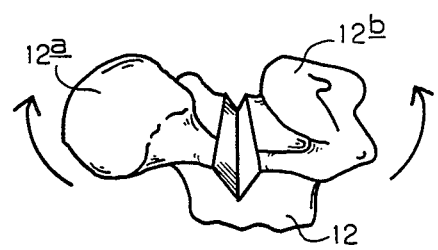
FIG. 8 is a fragmentary top view of the schematic representation of FIG. 7.

FIG. 8 is a fragmentary, true-to-life, top view of the diverged/rotated femoral sections 12a and 12b. In the preferred embodiment, rotation about an axis generally paralleling the long axis of the femur is in the direction shown, i.e. the femoral neck is caudally torsed about the long axis of the femur. This caudal torsion is referred to as femoral neck retroversion. It will be appreciated that rotation to a different extent or in a different direction, i.e., anteversion, may be performed within the scope of this invention. FIG. 8 shows, incidentally, the natural curvature of the femur in its proximal region 12.

Figure 9:
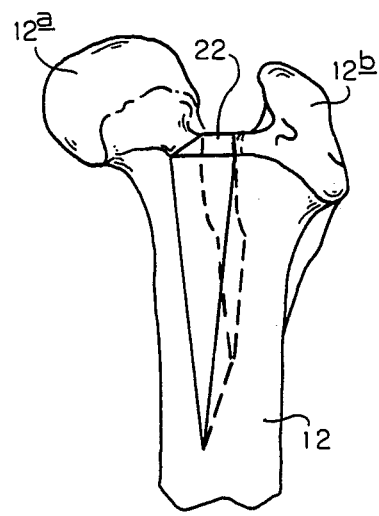
FIG. 9 is similar to FIG. 5, except that it shows a modification to the preferred method of practicing the invention in which a caudally and distally tapering wedge is inserted between the cut/diverged/rotated femoral portions.

Reference to FIG. 9 reveals a late stage in the practice of this modification. Either during or after diverging and rotating the femoral sections 12a and 12b, a distally and caudally tapering wedge 22 is inserted between them. It will be appreciated that, as described above in relation to wedge 18, wedge 22 need not extend the entire length of the cut. It will also be appreciated that wedge 22 may instead distally and cranially taper to effect rotation in a different direction, i.e., to effect anteversion. The important difference between this illustration and that of FIG. 5 will be appreciated as involving rotation as well as divergence of the femoral bone sections.

As the final step (not shown) in practicing this modification, the two cut, diverged and relatively rotated femoral sections are fixed by the method described above, or by any appropriate method.

The advantages offered by the invention should be apparent to those skilled in the art. Treatment, as by a single, preferably planar cut, is required to prepare the proximal portion of the femur for relative adjustment of the resulting joined, relatively movable sections. Once a desired configuration is produced, as by diverging and relatively rotating the femoral sections over a predetermined distance and through a predetermined angle, the femoral sections are fixed by conventional methods. By this osteotomy procedure, the length of the femoral neck and the torsional formation of the proximal femur may be altered, for example, to stabilize the coxofemoral joint.

Accordingly, while a preferred method of practicing the invention and a modification thereof have been described herein, it is appreciated that further modifications are possible that come within the scope of the invention.

It is claimed and desired to secure by Letters Patent:

1. A method of performing a biomechanical femoral neck-lengthening osteotomy comprising:
    treating the proximal end of the femur in such manner as to permit increasing the distance between the femoral head and the greater trochanter;
    adjusting the proximal end of the femur in such manner that the distance between the femoral head and the greater trochanter is increased; and
    fixing such adjusted sections against further movement relative to one another.

2. The method of claim 1, wherein said treating is performed by producing at least one cut.

3. The method of claim 1, wherein said adjusting is performed by diverging.

4. The method of claim 1, wherein said adjusting is performed by rotating such sections relative to one another about at least one axis which generally parallels the long axis of the femur.

5. The method of claim 1, wherein said adjusting is performed by diverging such sections and rotating the same relative to one another about at least one axis which generally parallels the long axis of the femur.

6. A method of performing a biomechanical femoral neck-lengthening osteotomy comprising:
    producing a cut in the proximal end of the femur, such cut being generally parallel with the sagittal plane, substantially to bisect the proximal end of the femur over a predetermined distance to create relatively movable sections;
    diverging the two thus-created sections, whereby the distance between the femoral head and the greater trochanter is increased; and
    fixing the two thus-diverged sections against further movement relative to one another.

7. The method of claim 6, wherein said diverging is performed by wedging.

8. A method of performing a biomechanical femoral neck-lengthening and neck-torsing osteotomy comprising:
    producing a cut in the proximal end of the femur, such cut being generally parallel with the sagittal plane, substantially to bisect the proximal end of the femur over a predetermined distance to create relatively movable sections;
    diverging the two thus-created sections, and rotating the same relative to one another about at least one axis which generally parallels the long axis of the femur, whereby the distance between the femoral head and the greater trochanter is increased and the angular relationship between the femoral head and the greater trochanter is altered; and
    fixing the two thus-diverged and relatively rotated sections against further movement relative to one another.

9. The method of claim 8, wherein said diverging is performed by wedging.

10. The method of claim 8, wherein said relative rotating is performed by wedging.

11. The method of claim 8, wherein said diverging and said relative rotating are performed by wedging.

* * * * *